US00PP26786P3

(12) United States Plant Patent
Jiménez

(10) Patent No.: US PP26,786 P3
(45) Date of Patent: May 31, 2016

(54) ***DRACAENA REFLEXA* PLANT NAMED 'RDLANIVAR'**

(50) Latin Name: *Dracaena reflexa*
Varietal Denomination: RDLANIVAR

(71) Applicant: Mario Pacheco Jiménez, San José (CR)

(72) Inventor: Mario Pacheco Jiménez, San José (CR)

( * ) Notice: Subject to any disclaimer, the term of this patent is extended or adjusted under 35 U.S.C. 154(b) by 47 days.

(21) Appl. No.: 14/544,134

(22) Filed: Nov. 28, 2014

(65) Prior Publication Data

US 2015/0150173 P1 May 28, 2015

(30) Foreign Application Priority Data

Nov. 28, 2013 (QZ) ..... PBR 2013/3028

(51) Int. Cl.
*A01H 5/00* (2006.01)

(52) U.S. Cl.
USPC ..... Plt./383

(58) Field of Classification Search
USPC ..... Plt./383
CPC ..... A01H 5/00; A01H 5/12
See application file for complete search history.

*Primary Examiner* — Kent L Bell
(74) *Attorney, Agent, or Firm* — Samuel R. McCoy, Jr.

(57) ABSTRACT

'RDLANIVAR' is a new and distinctive variety of *Dracaena reflexa* which is characterized by distinctive foliage variegation pattern in combination with unique colors of the foliage, unlike other *Dracaena reflexa* cultivars known to the Inventor, as well as long narrow leaves. The new variety is a *Dracaena*, typically produced as an indoor ornamental plant.

4 Drawing Sheets

Latin name of the genus and species: The Latin name of the genus and species of the novel variety disclosed herein is *Dracaena reflexa.*

Variety denomination: The inventive variety of *Dracaena reflexa* disclosed herein has been given the variety denomination 'RDLANIVAR'.

BACKGROUND OF THE INVENTION

The present invention relates to a new and distinct cultivar of *Dracaena reflexa*, which has been given the variety denomination of 'RDLANIVAR'. Its market class is PLT/383.

PARENTAGE

The new cultivar is the product of chance discovery. The new variety originated as a naturally occurring mutation, whole plant of *Dracaena reflexa* 'Anita'. The new variety was first discovered by the inventor, Mario Pacheco Jiménez, a citizen of Costa Rica, in August of 2009, at a nursery in Los Lagos, Costa Rica. After identifying the new variety as a potentially interesting selection, the inventor continued confidential testing and propagation of 'RDLANIVAR', assessing stability of the unique characteristics of this variety.

ASEXUAL REPRODUCTION

Asexual reproduction of the new cultivar 'RDLANIVAR' by way of vegetative cuttings was first performed at the same nursery in Los Lagos, Costa Rica during the period of September 2009 to March 2010. At least three subsequent generations have been produced from vegetative cuttings and have shown that the unique features of this cultivar are stable and reproduced true to type.

SUMMARY OF THE INVENTION

The cultivar 'RDLANIVAR' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Dracaena reflexa* cultivar 'RDLANIVAR'. These traits, in combination, distinguish 'RDLANIVAR' as a new and distinct cultivar.

1. *Dracaena* 'RDLANIVAR' exhibits foliage variegation with narrow, golden yellow centrally-axial stripes and broad, dark green marginally-axial stripes, when grown under medium light levels.
2. *Dracaena* 'RDLANIVAR' exhibits foliage variegation with broad, golden yellow centrally-axial striations and narrow, yellow-green marginally-axial striations, when grown under high light levels.
3. *Dracaena* 'RDLANIVAR' exhibits very long, narrow leaves.

Figure 1:
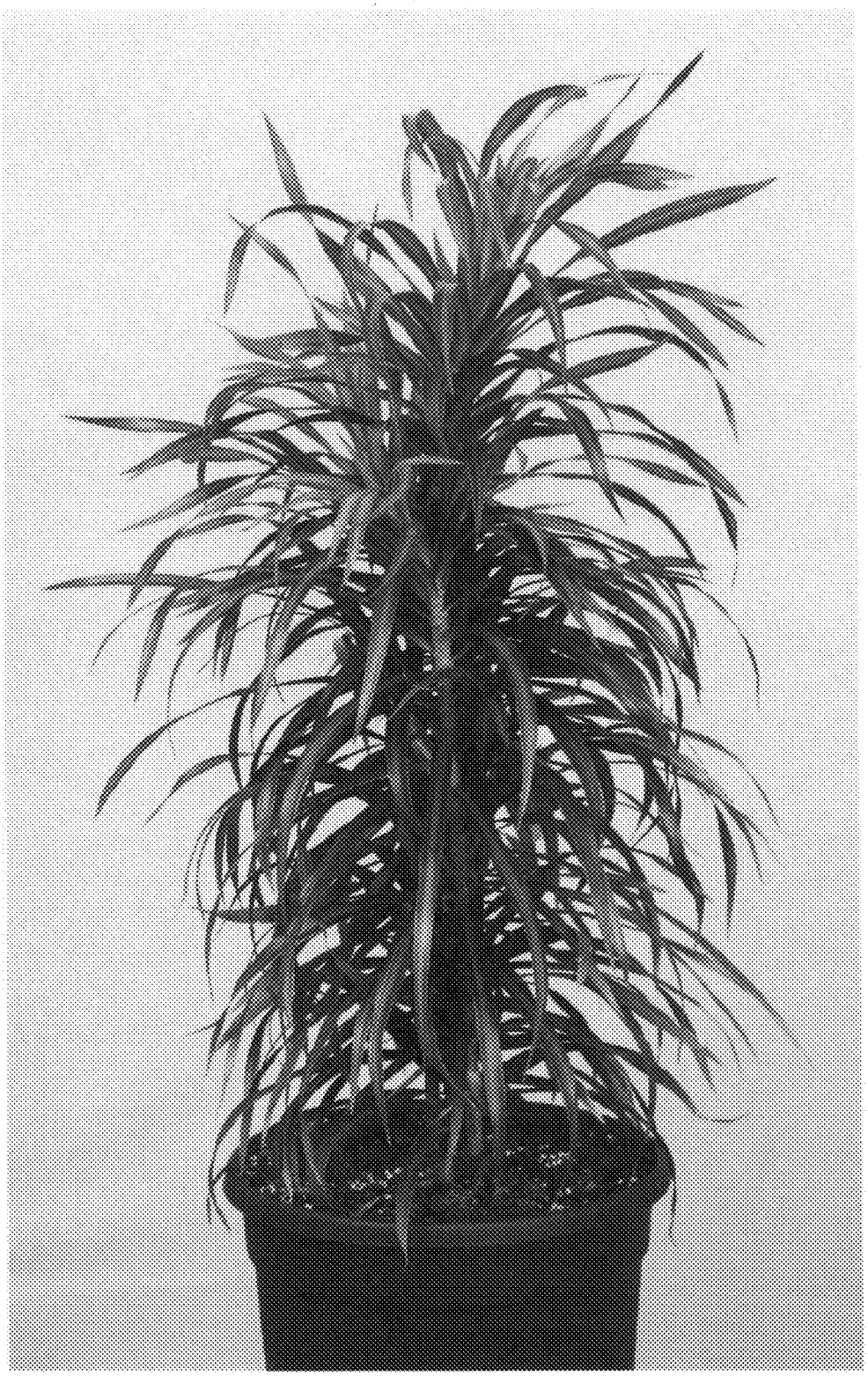
FIG. 1 shows, as nearly true as it is reasonably possible to make the same in color illustrations of this type, the typical foliage and growth characteristics of the new cultivar, 'RDLANIVAR' when produced under medium light levels. The plant shown is approximately 12 months old from a rooted cutting, potted into a 28 cm nursery pot, grown in a climate-controlled greenhouse in Roelofarendsveen, the Netherlands.
Figure 2:
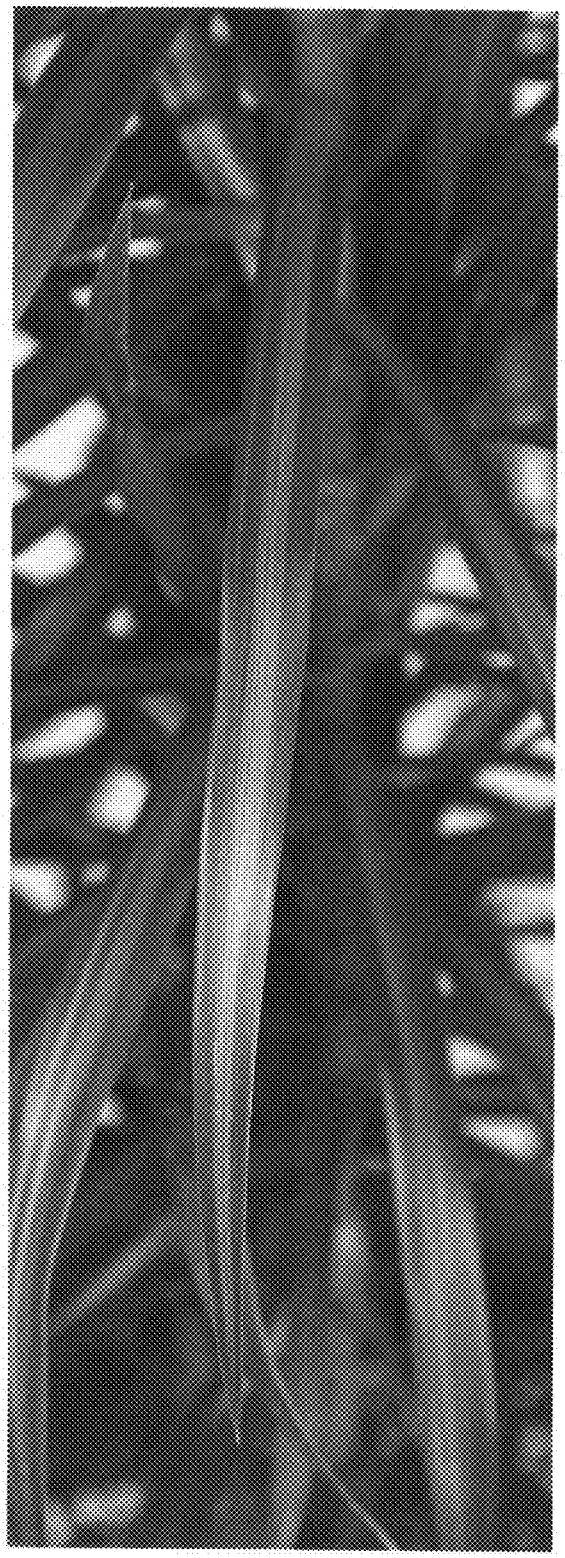
FIG. 2 shows, in full color, the typical foliage variegation of the plant in FIG. 1.
Figure 3:
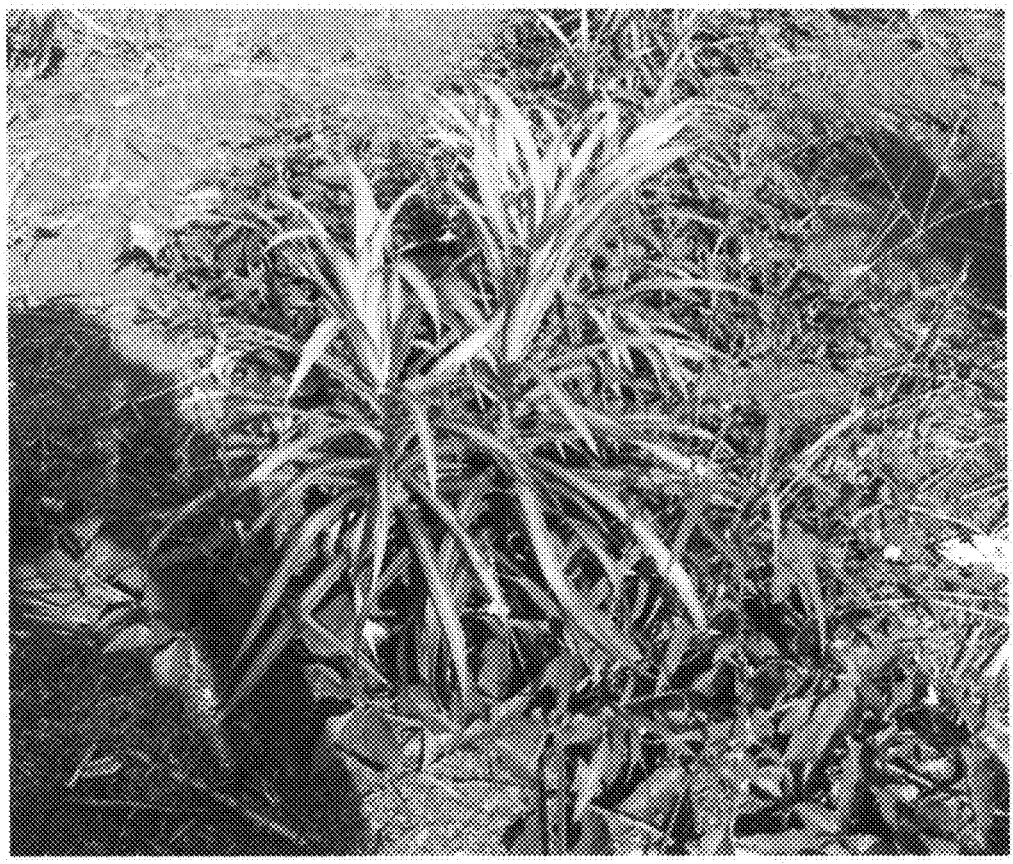
FIG. 3 shows, as nearly true as it is reasonably possible to make the same in color illustrations of this type, the typical foliage and growth characteristics of the new cultivar, 'RDLANIVAR' when produced under high light levels. The plant shown is approximately 8 months old, grown in full sun at a nursery in Los Lagos, Costa Rica.
Figure 4:
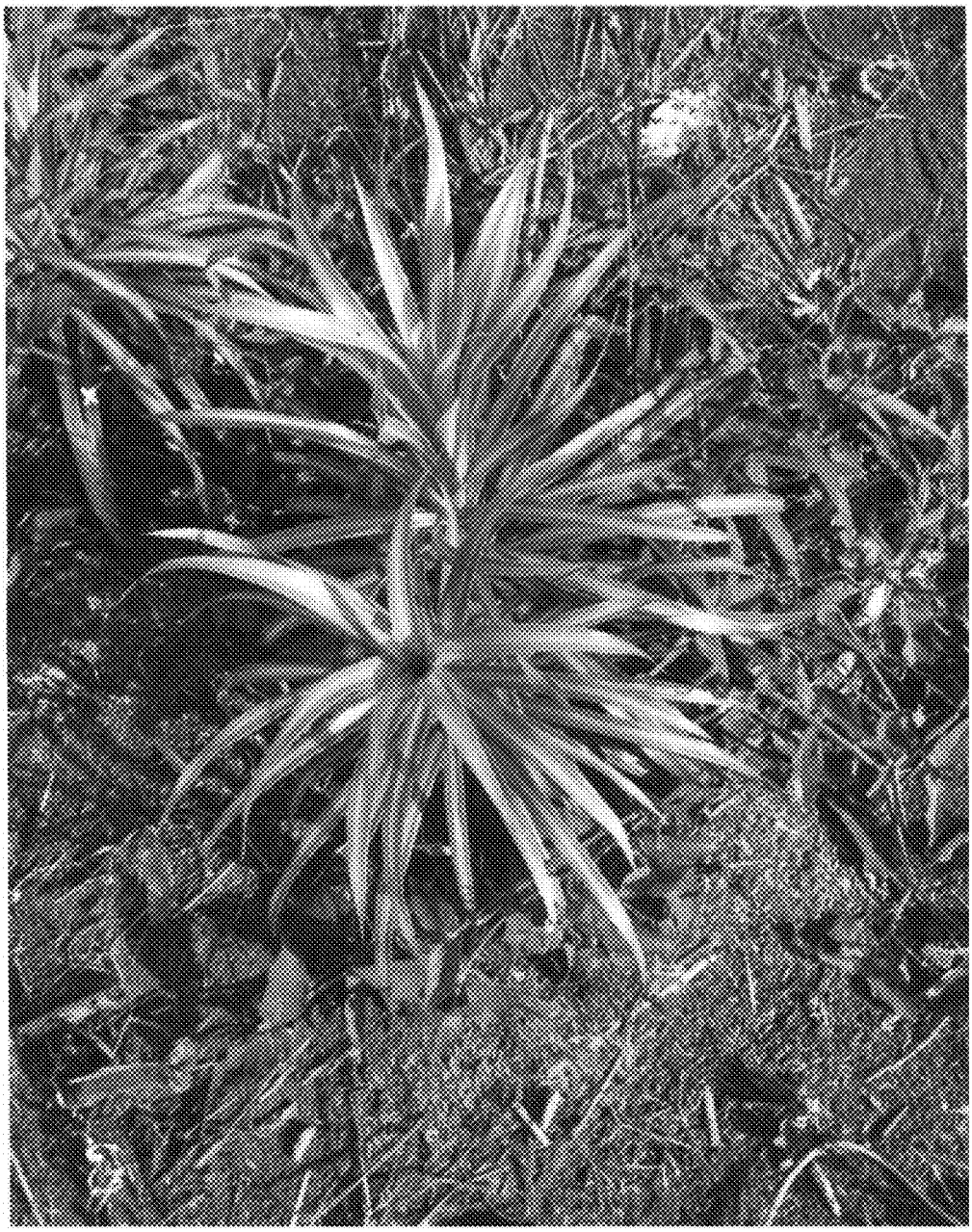
FIG. 4 shows, in full color, an overhead view of the plant in FIG. 3. Of note is the generally golden yellow appearance of leaf variegation.

The photographs were taken using conventional techniques and although colors may appear different from actual colors due to light reflectance it is as accurate as possible by conventional photographic techniques.

BOTANICAL DESCRIPTION OF THE PLANT

The following is a detailed botanical description of a new and distinct variety of *Dracaena reflexa* known as 'RDLANIVAR', based upon observations of plants, approximately 12 months old from a rooted cutting, potted into a 28 cm nursery pot, grown in a climate-controlled greenhouse in Roelofarendsveen, the Netherlands. Temperatures ranged from 22 to 30 degrees Celsius during the day and 17 to 22 degrees Celsius at night. No artificial light, photoperiodic treatments or chemical treatments were given to the plants. Observation data was recorded in November of 2014.

Those skilled in the art will appreciate that certain characteristics will vary with older or, conversely, with younger plants. 'RDLANIVAR' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2007 edition.

A botanical description of 'RDLANIVAR' and comparisons with other varieties of *Dracaena reflexa* are provided below.

TECHNICAL DESCRIPTION OF THE VARIETY

General plant description:

- *Growth rate*.—Moderate, approximately 10 cm per month.
- *Growth habit*.—Upright; not free branching, typically growing with main stems from the base of the plant.
- *Plant shape*.—Narrow, obovate.
- *Height*.—Average 73.6 cm in height.
- *Width*.—Average 55.2 cm in width.
- *Hardiness*.—USDA Zone 10.
- *Propagation*.—Vegetative cuttings.
- *Time to initiate roots*.—Approximately 6 weeks to initiate roots at 25 to 28 degrees Centigrade.
- *Environmental tolerances*.—Adapt to medium to high light levels; high drought tolerance once established; adapt to a wide range of soil types. Low salt tolerance.
- *Pest resistance and susceptibility*.—Not susceptible to any detrimental pests or diseases.

Root system: Moderately thick, moderately fibrous, not fleshy, young roots cream-white, older roots Greyed-Orange 163D.

Stems:

- *Branching characteristics*.—Not freely branched in nature; develops lateral branches only when manipulated by man by way of pruning. Naturally produces a small number of main stems arising from the plant's base.
- *Number of main stems*.—Three.
- *Stem strength*.—Very strong.
- *Stem diameter*.—Average 0.9 cm.
- *Internode length*.—Average 0.7 cm.
- *Stem texture*.—Glabrous, matte.
- *Stem color*.—Green, near RHS 143B to 143C, slightly striped axially yellow-green; near RHS 144B. Older stems grey-brown; near RHS 199A, slightly striped lighter axially; near RHS 199D.
- *Quantity of leaves per stem*.—Average 73.

Foliage:

- *Leaf attachment*.—Sheathing.
- *Leaf arrangement*.—Alternate (spirally).
- *Leaf attitude*.—Leaves in an average angle of 80° to stem (=0).
- *Texture (adaxial surface)*.—Glabrous, moderately glossy.
- *Texture (abaxial surface)*.—Glabrous, moderately glossy to glossy.
- *Leaf shape*.—Lorate, slightly twisted.
- *Leaf apex*.—Long and narrow acuminate.
- *Leaf base*.—Broad cuneate.
- *Leaf length*.—Average 26.1 cm in length.
- *Leaf width*.—Average 1.6 cm in width.
- *Leaf margin*.—Entire, very slightly and coarsely undulate.
- *Immature leaf color (adaxial surface) when grown under medium light levels*.—Yellow-green; near RHS 144A, with a broad lighter axially central stripe; near RHS 145A and 145B and 150B.
- *Immature leaf color (abaxial surface) when grown under medium light levels*.—Yellow-green; near RHS 144A, with a broad lighter axially central stripe; in between near RHS 145A and 145B and 150C.
- *Immature leaf color (adaxial & abaxial surfaces) when grown under high light levels*.—Same as when grown under medium light only said axial central stripes are broader.
- *Mature leaf color (adaxial surface) when grown under medium light levels*.—Green to greyed-green; in between near RHS 139A and N189A but darker, with a broad green axially central stripe; near RHS 143A, 143B and in between 139A and N189A but darker.
- *Mature leaf color (abaxial surface) when grown under medium light levels*.—Green; near RHS N137D, with a broad green to yellow-green axially central stripe; near RHS 137B and 144A.
- *Mature leaf color (adaxial surface) when grown under high light levels*.—Yellow-green; near RHS 144A, with a broad lighter axially central stripe; near RHS 145A and 145B and 150B.
- *Mature leaf color (abaxial surface) when grown under high light levels*.—Yellow-green; near RHS 144A, with a broad lighter axially central stripe; in between near RHS 145A and 145B and 150C.
- *Sheath dimensions*.—Approximately 0.4 cm long and 1.3 cm wide.
- *Sheath texture (adaxial surface)*.—Glabrous; glossy.
- *Sheath texture (abaxial surface)*.—Glabrous; matte.
- *Sheath color (adaxial surface)*.—Yellow-green; near RHS 145B.
- *Sheath color (abaxial surface)*.—Near RHS 143B.
- *Vein pattern*.—Parallel.
- *Vein color (adaxial surface)*.—Same as surrounding leaf surface.
- *Vein color (abaxial surface)*.—Same as surrounding leaf surface.

Flower: Flowering has not been observed.

Reproductive organs: Reproductive organs have not been observed.

Seed and fruit: Seed production has not been observed.

Comparisons with parent plants: Plants of the new cultivar 'RDLANIVAR' are similar to parent 'Anita' in most horticultural characteristics including plant shape, plant dimensions and foliage dimensions. However, the foliage of 'RDLANIVAR' is variegated with unique foliage colors, whereas 'Anita' produces green leaves.

Comparisons with other commercial *Dracaena*: Plants of the new cultivar 'RDLANIVAR' are comparable to the commercial variety *Dracaena reflexa* 'Song of India' (unpatented), in that both have variegated foliage. However, the two varieties have different variegation patterns and colors. Also, the foliage colors of 'Song of India' are relatively unaffected by variations in light levels, whereas foliage colors of 'RDLANIVAR' become more golden yellow under higher light levels. Furthermore, leaves of 'Song of India' are generally short and broad, whereas leaves of 'RDLANIVAR' are long and narrow.

That which is claimed is:

1. A new and distinct variety of *Dracaena reflexa* plant named 'RDLANIVAR', substantially as described and illustrated herein.

* * * * *